(12) United States Patent
Rance et al.

(10) Patent No.: US 11,471,115 B2
(45) Date of Patent: Oct. 18, 2022

(54) SYSTEM AND METHOD FOR USING A WEARABLE DEVICE WITH BIOFEEDBACK SENSORS TO MITIGATE DISEASE TRANSMISSION

(71) Applicant: Tracklet Inc., Huntington Beach, CA (US)

(72) Inventors: John Stuart Rance, Huntington Beach, CA (US); Jose Aaron Gonzalez, McAllen, TX (US)

(73) Assignee: Tracklet Inc., Huntington Beach, CA (US)

( * ) Notice: Subject to any disclaimer, the term of this patent is extended or adjusted under 35 U.S.C. 154(b) by 0 days.

(21) Appl. No.: 17/581,701

(22) Filed: Jan. 21, 2022

(65) Prior Publication Data
US 2022/0225948 A1 Jul. 21, 2022

Related U.S. Application Data

(60) Provisional application No. 63/140,107, filed on Jan. 21, 2021.

(51) Int. Cl.
*G08B 21/02* (2006.01)
*A61B 5/00* (2006.01)
(Continued)

(52) U.S. Cl.
CPC ............ *A61B 5/746* (2013.01); *A61B 5/0022* (2013.01); *A61B 5/01* (2013.01); *A61B 5/1112* (2013.01);
(Continued)

(58) Field of Classification Search
CPC ......... A61B 5/746; A61B 5/0022; A61B 5/01; A61B 5/6802; A61B 5/7435; G08B 21/02; G08B 21/182
See application file for complete search history.

(56) References Cited

U.S. PATENT DOCUMENTS

| 11,056,242 B1 * | 7/2021 | Jain ......................... G16H 50/70 |
| 2009/0069642 A1 * | 3/2009 | Gao ....................... H04L 67/125 600/300 |

(Continued)

*Primary Examiner* — Benyam Haile
(74) *Attorney, Agent, or Firm* — Entralta; James F. Fleming; Peter D. Weinstein

(57) ABSTRACT

An apparatus and method for monitoring body temperature includes a temperature sensor configured to detect a body temperature of a user wearing a wearable device and produce a temperature signal representative of the detected body temperature. A transmitter is configured to send and receive signals including the temperature signal produced by the temperature sensor. Circuitry, which is coupled to the temperature sensor and the transmitter, is also coupled to a memory comprising a plurality of instructions. When those instructions are executed by the circuitry, the wearable device receives a plurality of temperature signals from the temperature sensor over a predetermined period of time and transmits the plurality of temperature signals to a server to determine a baseline temperature pattern for the user. A current temperature signal is then received from the temperature sensor and transmitted to the server. A user alert signal is received from the server when the current temperature signal differs from the baseline temperature pattern by a predetermined threshold, the user alert signal indicating a potential illness of the user.

18 Claims, 3 Drawing Sheets

(51) Int. Cl.
 *A61B 5/01* (2006.01)
 *G08B 21/18* (2006.01)
 *A61B 5/11* (2006.01)
(52) U.S. Cl.
 CPC .......... *A61B 5/6802* (2013.01); *A61B 5/7435* (2013.01); *G08B 21/02* (2013.01); *G08B 21/182* (2013.01)

(56) References Cited

U.S. PATENT DOCUMENTS

| | | | | |
|---|---|---|---|---|
| 2009/0076840 | A1* | 3/2009 | Boyden | G16H 40/67 |
| | | | | 705/2 |
| 2016/0242656 | A1* | 8/2016 | Jackson | A61B 5/746 |
| 2021/0000347 | A1* | 1/2021 | Stump | A61B 5/11 |
| 2021/0330190 | A1* | 10/2021 | Arwari | A61B 90/98 |

* cited by examiner

SYSTEM AND METHOD FOR USING A WEARABLE DEVICE WITH BIOFEEDBACK SENSORS TO MITIGATE DISEASE TRANSMISSION

PRIORITY

This application claims priority to provisional application 63/140,107 filed on Jan. 21, 2021. This application incorporates by reference

BACKGROUND

Field

This disclosure relates to field of detecting temperatures and to an apparatus and method for detecting, communicating, and evaluating human temperature variations.

Description of the Related Art

As viruses like Covid-19 become more prevalent across the world, the importance of maintaining a safe environment has also become more important. Maintaining a safe environment becomes more important and more challenging when the environment involves groups of people in close proximity to each other. For example, it is difficult for employers and hosts overseeing hotels, cruise ships, concerts, sporting events, and large offices to ensure that people suffering from an illness avoid coming to the venue and risk infecting others.

Even if it is possible to identify a person with a potential illness, such as Covid-19, an additional problem for an employer or host lies in being able to quickly communicate with that person having the illness. Likewise, an employer or host may also be unable to quickly select a course of action when learning of the person with the potential illness. It would therefore be helpful to have a system that makes it possible for employers and hosts to identify persons with a potential illness and keep them away from the location of the employer or host.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
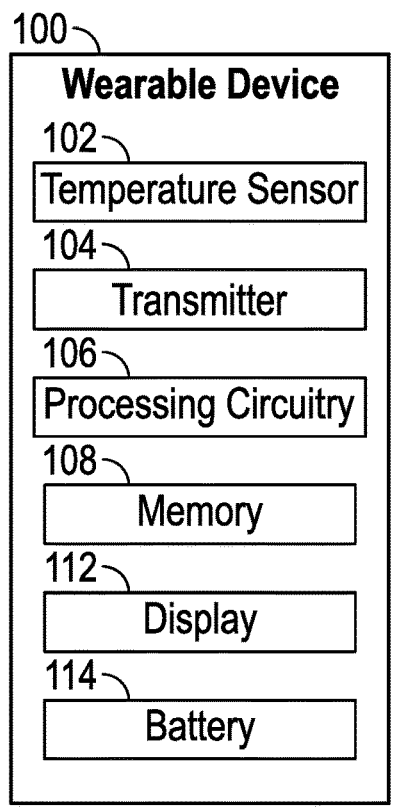
FIG. 1 shows an exemplary wearable device according to an embodiment.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced using one or more implementations. In one or more instances, structures and components are shown in simplified form in order to avoid obscuring the concepts of the subject technology.

In the drawings referenced herein, like reference numerals designate identical or corresponding parts throughout the several views or embodiments.

While traditional thermometers or devices like Fitbit can deliver temperature readings directly to a user, these devices do not track temperature readings nor provides reports, such as through an IP switch/server, to an employer/host and/or an employee/guest. According to an embodiment, such temperature readings can be tracked, reported, stored, accessed, and analyzed so that the information can be accessed in a database by the employer or host. In addition, the IP switch can be configured to gather body temperature data and apply a protocol to determine if instructions need to be delivered to the employee or guest. To ensure protecting the privacy of the employee or guest, this information can be collected only from willing employees or willing guests. Any employee or guest can elect not to participate.

But with participation by a substantial number of employees and guests for the benefit of the other employees and guests, the employer or host can monitor the body temperature of employees and guests and evaluate whether a change or spike in body temperature reveals a likely illness. Based on this evaluation, the employer or host can alert the employee or guest to remain home and avoid potentially infecting other employees or guests.

Thus, according to an embodiment, an employer or host can be informed continuously, through remote communication, regarding the body temperature of employees or guests and evaluate and determine a potential illness. Absent this ability, determining the body temperature of a person typically required the employer or host to stop that person at an entry at the venue (e.g., office or hotel) and measure the body temperature there with a thermometer or other measurement device. Instead, according to the embodiment, each employee or guests can wear a body temperature-sensing device, such as on the wrist of the person, so that the employer or host has advanced notice of the body temperature of the arriving employee or arriving guest and potentially advise the employee or guest to remain home or seek medical attention. This monitoring keeps track of the body temperature of the employee or guest over any relevant period so that the employer or host can be alerted of a significant body temperature change of the employee or guest.

According to an embodiment, an employer can monitor employees regardless of location to detect significant spikes or changes in the body temperature of their employees who may be coming and going to the employer's place of business. Similarly, a host, such as a hotel operator, airline operator, or cruise ship director, can monitor guests regardless of location to detect significant spikes or changes in the body temperature of the guests who may be coming and going to the host's venue. In one implementation, the monitoring and detection can include an Internet Protocol (IP) telecommunications switch and an application installed on a smartphone or other mobile device. The application can be configured to collect the body temperature data from a temperature sensing chip or other body temperature measuring element that is installed next to the skin, such as on the wrist, via a communication protocol such as near field communication module (NFC), Bluetooth, WiFi, or other protocol capable of sending data between a wearable device and a mobile device.

In addition to body temperature, the application can also collect other relevant data, such as a location where the body temperature was measured and an identifier of the person whose body temperature is being sensed. The location can be provided by a GPS circuit or RFID chip included in a wearable device in which the body temperature sensors in installed to detect body temperature. The identifier is preferably a value that is stored on the wearable device and/or the mobile device associated with the wearable device and is uniquely associated with the user of the wearable device/mobile device so that all of the body temperature data provided by the wearable device from the body temperature sensor can be associated with that user. After the application, preferably operating on a mobile device, has collected the body temperature data from the wearable device using the application communication protocol, the application can be configured to pass the data to an IP switch that passes the data to a database or cloud, such as on one or more servers. The body temperature data can be collected over an adjustable time period, such as a day, a week, or a month, and can be used to create a body temperature baseline for the user.

In addition to NFC, the temperature sensing chip can also communicate via Bluetooth or other proximate or nearby communication protocol to the application. The temperature sensing chip is preferably part of a wearable device, such as a bracelet, that can be battery powered and continuously report temperature data to the application on the user's smartphone or mobile device, which can then relay the data to the server. Alternatively, the wearable device can be a smartwatch or other computerized device that is capable of operating the application and communicating directly with a server, such as through cellular or WiFi communications. The temperature sensing chip preferably includes an NFC or Bluetooth module built-in that is capable of broadcasting data to the application in the mobile device when the wearable device and mobile device are in close proximity. Alternatively, a small, thin chip and NFC or Bluetooth antenna can be installed on an existing wristwatch to thereby enable the wristwatch to broadcast biometric data to the application.

With the body temperature baseline available, subsequent data feeds collected from the body temperature sensing chip and the application can be reviewed by the server and database connected via the IP switch. Based on the review, the server can be configured with a predetermined protocol to determine if an SMS or VoIP communication should be sent to the user and/or the employer or host of the user. The IP switch preferably includes at least one server and at least one voice-enabled internet gateway, which is connected to the internet. The IP switch, and all parts of the IP switch, can be installed with proprietorially written software that operates the protocols and databases described in more detail herein.

FIG. 1 shows an exemplary wearable device according to an embodiment. As shown in FIG. 1, a wearable device 100 includes a body temperature sensor 102, a transmitter 104, a processing circuitry 106, a memory 108, a display 112, and a battery 114. Wearable device 100 can be, for example, a wrist bracelet with sensor 102, transmitter 104, processing circuitry 106, memory 108, display 112, and battery 114. Alternatively, wearable device 100 can be a wristwatch or smartwatch configured to include the same elements. Wearable device 100 can also be configured to be any other shape or form capable of being worn by a user, configured to include the elements shown in FIG. 1, and capable of being positioned so that the body temperature sensor 102 can properly measure the user's body temperature.

Body temperature sensor 102 can be a chip, circuit, or sensor that is configured to detect a body temperature of a user when sensor 102 is, for example, next to or adjacent to a skin surface of the user. Sensor 102 is preferably configured to generate a body temperature signal indicative of the detected body temperature. Transmitter 104 can be, for example, an antenna and configured to transmit signals and data from wearable device 100. Transmitter 104 can alternatively be configured as a transceiver that is configured to both transmit and receive signals. The signals and data can be transmitted from transmitter 104 using communication standards as are known to one skilled in the art including, for example, Nearfield Communication (NFC), Bluetooth, WiFi, or cellular communication. When implemented with NFC or Bluetooth, the signals and data can be received and read when the wearable device 100 is proximate to a mobile device, such as a smart phone, mobile phone, tablet, or laptop, or proximate to a reader. When implemented with WiFi or cellular, the signals and data can be received and read from the wearable device 100 without the same distance limitations.

Processing circuitry 106 can include circuitry, such as a microprocessor, microcontroller, CPU, memory, RAM, and/or ROM, that can be configured to control all of the operations of wearable device 100 including controlling the operations of the body temperature sensor 102, transmitter 104, memory 108, display 112, and battery 114. Processing circuitry 106 can also include GPS circuitry that generates location data according to the position of wearable device 100. Memory 108 can be a RAM, ROM, and/or other memory circuit capable of receiving, storing, and providing data and instructions that can be used by processing circuitry 106 to perform functions of wearable device 100. Although not shown in FIG. 1, wearable device 100 can also include the use and placement of a Radio Frequency Identification (RFID) chip, which can be used to allow or deny access to the user of the wearable device 100 to locations or venues, as well as provide location data and a unique identifier for the wearable device 100 and/or user.

Display 112 can be, for example, an LCD or LED display that presents information and data to a user of wearable device 100. Display 112 can display information regarding body temperature, display an alert signal when body temperature shows an abnormal deviation, display questions to verify the likely presence or absence of an illness, provide touchscreen capabilities to enable a user to provide responses to the questions with a touch input, and display instructions to the user. Battery 114 is configured to provide power to components for wearable device 100. Battery 114 preferably has at least a 6-18 month lifespan for powering wearable device 100 before needing replacement. Battery 114 can also be a rechargeable battery. Battery 114 can be recharged, such as by connecting wearable device 100 directly or indirectly to a power source, or can be charged kinetically through motion of wearable device 100.

Wearable device 100 can be configured to capture data continuously, at specific times or periods, or in response to a request or user input. When capturing data continuously, for example, a user preferably has wearable device 100 nearby to a mobile device, such as a smartphone, that has an application linked to the operation of wearable device 100 that can store several hours or more of temperature readings from the user.

Wearable device 100 is preferably configured to be waterproof such as for showering, pool usage, or spills, to enable continuous body temperature monitoring. Wearable device 100 is also preferably designed to be comfortable for extended wear, e.g., for 30 days, and can be formed with silicone or similar material that makes extended wear more comfortable as well as preferably being hypoallergenic and adjustable.

Figure 2:
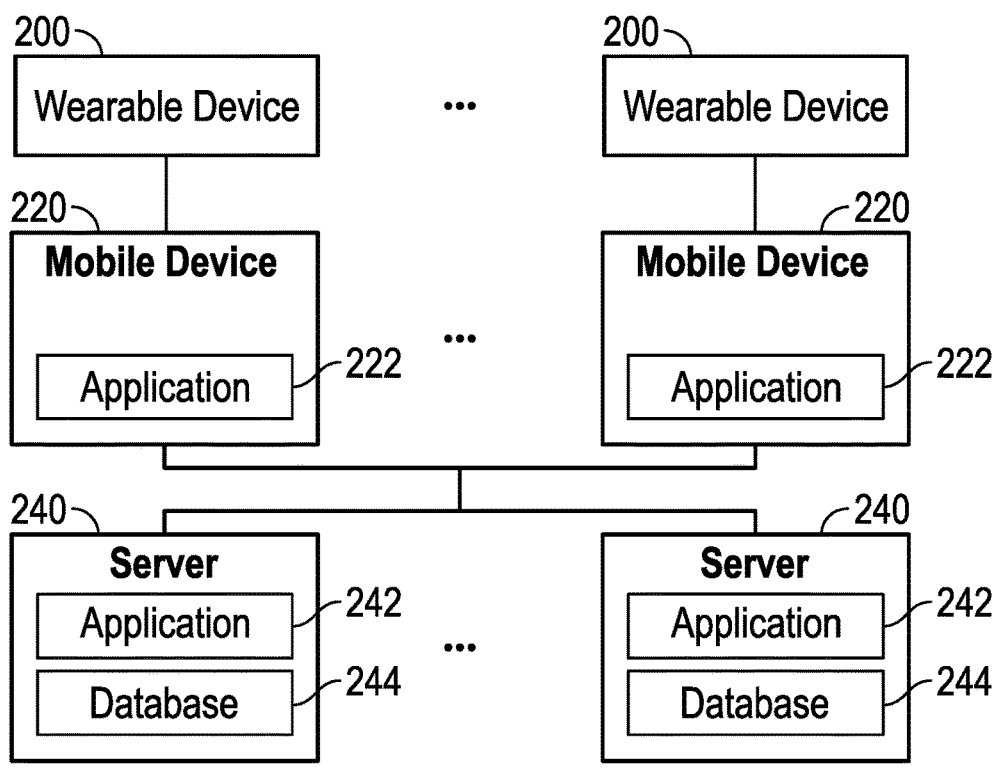
FIG. 2 shows an exemplary reporting and monitoring system according to another embodiment.

FIG. 2 shows an exemplary system comprising wearable devices, mobile devices, and servers according to an embodiment. As shown in FIG. 2, the system can include multiple wearable devices 200, multiple mobile devices 220, and multiple servers 240. Although multiple wearable devices 200, multiple mobile devices 220, and multiple servers 240 are shown in FIG. 2, it should be understood that the system can include just one of each instead of multiple ones of each. Wearable devices 200 in FIG. 2 can be configured in the same manner and have the same functionality as wearable device 100 in FIG. 1. Accordingly, further description of wearable device 200 is omitted.

Mobile device 220 can be a smartphone, mobile phone, tablet, laptop, or other mobile computing device capable of communicating with other devices and running applications. Mobile device 220 preferably includes processing circuitry and memory or storage configured to operate the mobile device, control the sending and receiving of data and signals, and running one or more applications including application 222. Mobile device 220 can send and receive data from wearable device 200 using, for example, NFC, Bluetooth, WiFi, or cellular communication.

Application 222 can be a bidirectional tool that collects the data provided by a body temperature sensor in wearable device 200. All of the body temperature data collected by application 222 can be timestamped with the time and date of the collection along with other relevant data including an identifier for the user of wearable device 200 providing the body temperature data and a location of that user, thereby providing a real-time representation at the moment of collection. Application 222 can be configured to control mobile device 220 to send the collected data to one or more of servers 240.

Server 240 can be a computing device capable of communicating with other devices and running applications. Server 240 preferably includes processing circuitry and memory or storage configured to operate the server, control the sending and receiving of data and signals including over the Internet, through WiFi, and/or through cellular communication, and run one or more applications including application 242. Server 240 can send and receive data from wearable device 200 and/or mobile device 220 using, for example, WiFi or cellular communication.

Application 242 can be configured to be event driven, operate in real-time, and use database programming such as NoSQL or bigdata. Application 242 can also be configured with REST or representational state transfer to control data transfer between application 222 and servers 240, as well as between servers 240 and a computing device operated by users, employers, hosts, medical facilities, or other entity entitled to have access to the stored body temperature and other related data in database 244. In addition, server 240 can include Kafka internal modules, which is a message broker designed to quickly and efficiently move large amounts of data packets between message queues following specified business rules. Server 240 can also be configured to operate as an IP switch and/or VOIP platform to provide SMS messaging, interactive voice response (IVR) capabilities, and/or live person voice communication.

In operation, applications 242 in servers 240 collects the body temperature data for each individual user of wearable device 200, along with other related data such as location, time, and user identifier, and stores the data in one or more databases 244. All of the data can be provided into a contemporaneous data model for processing, such as by a machine learning algorithm.

Figure 3:
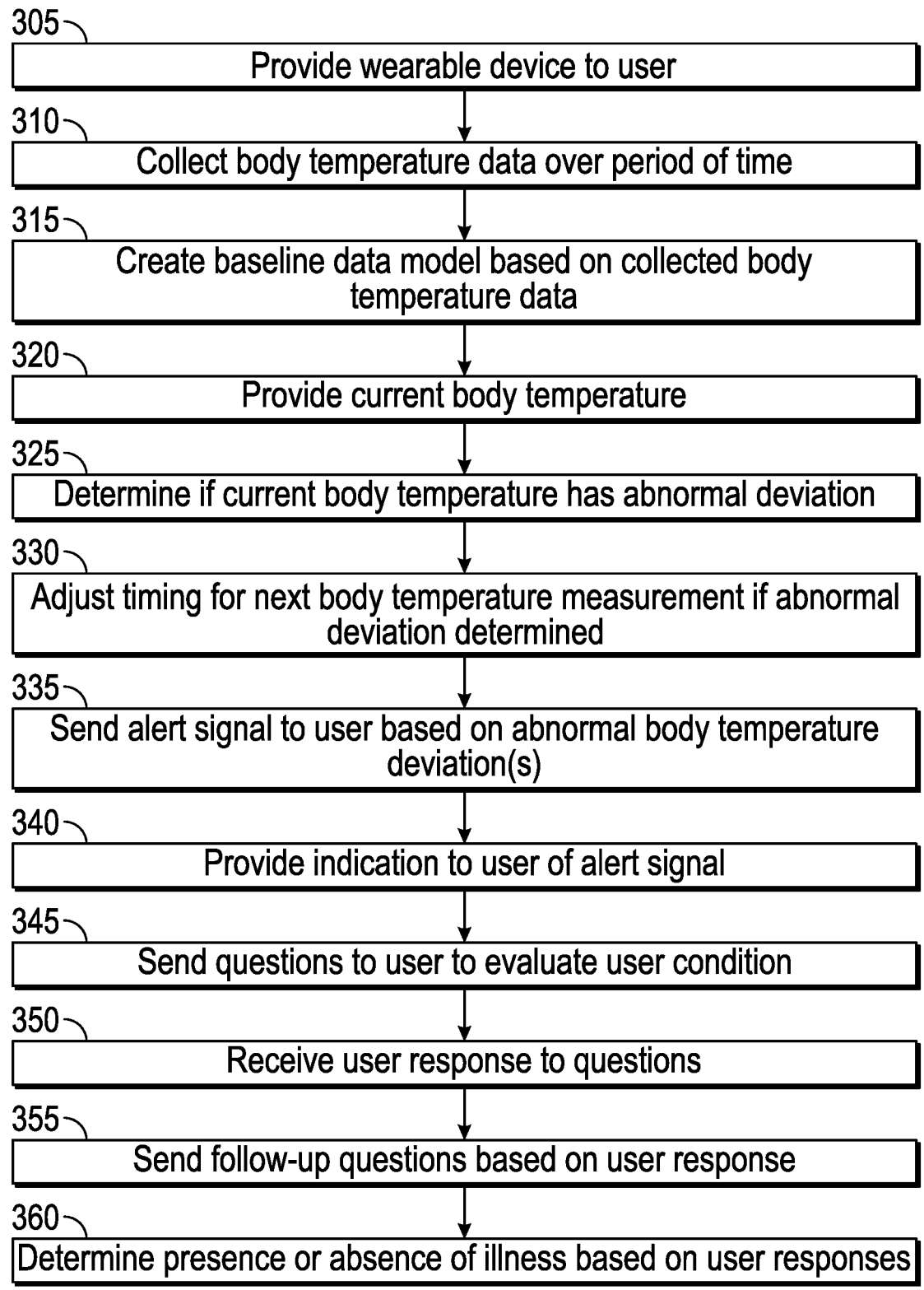
FIG. 3 is a flow chart of reporting and monitoring according to an embodiment.

FIG. 3 is a flow chart for tracking body temperature according to an embodiment. As shown in FIG. 3, a user can be furnished with a wearable device, such as wearable device 100 (step 305). The wearable device 100 can be provided to the user by an employer or host. For example, the employer may want to know details about the body temperature of each and every employee, whereas the host of a cruise ship, hotel, or concert venue may similarly desire to know the body temperature of any person that may be a guest.

Once the user starts wearing the wearable device 100, body temperature data for the user can be collected over a certain period (step 310). For example, once the user begins wearing the wearable device 100, body temperature data can be collected for at least one day, one week, one month, multiple months, or any period sufficient to determine a body temperature pattern for that user. In addition to the body temperature data, the data collected preferably includes a time at which the body temperature was sensed, a location at which it was sensed, and an identifier for the user. The collected data can be provided from the wearable device 100 to a corresponding application 222 on a mobile device 220, which then provides the data to a corresponding one or more applications 242 on one or more servers 240 for storage in one or more databases 244.

The data collected over the period can be used to create a data model unique to each individual user (step 315). The data model includes a baseline temperature model that accounts for the time of day and location and the user. The data model including the baseline temperature model can be developed by the application 222 running on mobile device 220 and/or application 242 running on server 240.

The baseline temperature model provides a basis for comparing a current body temperature data of the user to determine if the current body temperature indicates an abnormal deviation. The data model also includes sufficient data points to be able to predict if a particular individual user may experience an increase in body temperate over a subsequent period of time, such as a few hours. In addition, the data model can include information that uses incoming real-time data to predict temperate deviations outside of the user's normal temperature pattern as represented by the baseline temperature model. All data received can be fed into the data model in real-time. The data model can account for the normal variation pattern exhibited by the human body. For example, it is known that a person's body temperate is higher during waking hours and lower during a period of sleep or rest. Other factors also contribute to a person's specific body temperature at any given moment, such as activity level, ambient temperature, alcohol intake, etc.

Once a user has begun to submit data over the certain period for creating the data model including the baseline temperature model, a current body temperature can be provided from the wearable device for the user (step 320). Like the previously collected data, the data collected preferably includes the body temperature, a time at which the body temperature was sensed, a location at which it was sensed, and an identifier for the user. The currently collected data can be provided from the wearable device 100 to a corresponding application 222 on a mobile device 220, which then provides the data to a corresponding one or more applications 242 on one or more servers 240 for storage in one or more databases 244.

A determination is then made if the current body temperature has an abnormal deviation (step 325). The abnormal deviation can be, for example, that the current body temperature deviates from the baseline temperature model by a certain threshold, such as 0.5 degrees (Celsius or Fahrenheit), 1 degree, or other threshold as may be necessary to assess a potential illness of a user, such as a body temperature exceeding a certain value, e.g., 100 degrees Fahrenheit. This determination can be made, for example, by the processing circuitry 106 on wearable device 100, by the application 222 operating on mobile device 220, or by application 242 operating on server 240.

If an abnormal deviation is detected, a timing for a subsequent body temperature measurement can be shortened (step 330). By shortening the time between measurements, an increased amount of data can be collected in a time period, which allows for a more accurate determination to be made and correspondingly increases the effectiveness of the data models. In addition, the timing and criteria of data being sensed and sent from the wearable device 100 can be controlled by the host or the employer, for example, by communicating with server 240, which can respond to the communication to signal wearable device 100 directly or via application 222 on mobile device 220 to provide the data at the requested time.

Based on the detection of one or more determinations of abnormal body temperature deviations, an alert signal can be sent to the user (step 335). The alert signal can be sent, for example, from server 240 directly to wearable device 100 or from server 240 to wearable device 100 via mobile device 220. In response to the alert signal, the wearable device 100 provides an indication to the user of the alert (step 340). The indication can be, for example, a text message displayed on display 112 of wearable device 100, a sound, a haptic, an illumination, a voice message, or a live voice. The indication represents to the user that an abnormal deviation of body temperature has been detected, such as that the user's body temperature has deviated above a certain threshold, such as one degree. The abnormal deviation is indicative to the current and/or recently detected body temperatures deviating from a normal temperature, such as determined from the user's baseline body temperature model, by a certain amount or threshold. Typically, the deviation will be an increase or spike in the user's body temperature.

In addition to sending the alert signal, one or more questions can be sent to the user to verify if the abnormal deviation is indicative of an illness or other health issue (step 345). Like the alert signal, these questions can be sent, for example, from server 240 directly to wearable device 100 or from server 240 to wearable device 100 via mobile device 220. The questions explore the condition, location, and activity of the user to determine if there may be reasons for the abnormal deviation beyond illness. The user responds to the questions (step 350) and follow-up questions can be dependent on the user responses (step 355). Based on the answers to the questions, a determination is made that the user has or does not have an illness (step 360).

In any of the messages received by the user, an illumination signal can be provided from the server and ultimately displayed on the display 112. The illumination signal can be, for example, a red, yellow, or green color, with the color indicating a risk level of the user with red being highest risk and green being low risk or in the clear. This illumination can also be sent to and received by the employer or host along with location and identification information of the relevant user.

Throughout this process, server 240 and/or mobile device 220 can contact the user at established intervals depending upon the time of day. In addition, server 240 (including application 242) can be configured, for example, to detect usage of the mobile device 220, and if no body temperature data is received from the wearable device 100 after an established time, such as a certain number of minutes, server 240 can initiate contact via SMS messaging or VoIP telephone calls to ensure that any issues preventing body temperature data from being collected and sent can be remedied. Until the issues are remedied, server 240 can contact the user at a certain interval of time since the last report of body temperature. The SMS messaging or VoIP telephone call can remind the user, for example, to touch the wearable device 100 to their mobile device 220.

Both SMS messaging and VoIP telephone calls can be used. For example, after a first SMS message with no response from the user, server 240 can repeat the SMS message two hours later. At four hours with no data received, and following the guidance provided by the host or employer, server 240 can switch from SMS to VoIP telephone calls in an attempt to contact the user to reestablish the data collection from the wearable device 100 and application 222 of mobile device 220. If the user still fails to respond, server 240 can message the employer or host to report a rogue or incapacitated user and allow the employer or host to locate the user and take appropriate action. Each employer or host can also define the parameters on when they want to be contacted. For example, server 240 can report to the employer or host any alert condition and the last location of the user or the user's RFID tag.

The questions presented to a user after an alert signal are preferably designed to determine if there is a reason beside illness to explain the abnormal deviation in body temperature, such as through a series of dual choice questions. For example, "We have detected a one degree rise in your body temperature. Do you have a reasonable explanation for this increase? Please respond with a 1 for yes or 2 for no." A decision tree can be stepped through following the responses received from the user to a series of diagnostic questions. Each question and answer are designed to determine either the next question in sequence or initiate an event sequence leading to a physical examination of the user by designated medical personnel. For example, a point can be reached in the decision tree where illness is likely, at which point an employer can decide to bar the affected employee from the premises, such as by deactivating the employee's entry card, while sending the employee instructions on how to reach the company doctor's office. Similarly, a cruise ship operator can reach the decision to send medical personnel to a user's cabin.

Server 240, such as through operation of application 242, can examine the answers received from the user, and if the user does not have a reasonable explanation for the abnormal deviation in body temperature, server 240 can notify the employer or host to make direct telephone contact with the user to determine a course of action to protect the safety of the user and people in the area. If the employer or host has a sickbay or health services department, then server 240 can also initiate a recorded phone call between the two parties. For example, on a cruise ship, server 240 can start a voice call to the affected user's stateroom, and then the user can be conferenced in with the sickbay on the ship or with some other health professional designated by the host. Server 240 can also ask the user via SMS message if the affected user can get to the sickbay or designated health facility or initiate an IVR VoIP phone to contact the user directly with this question if server 240 does not receive a response to the question in the SMS message.

Figure 4:
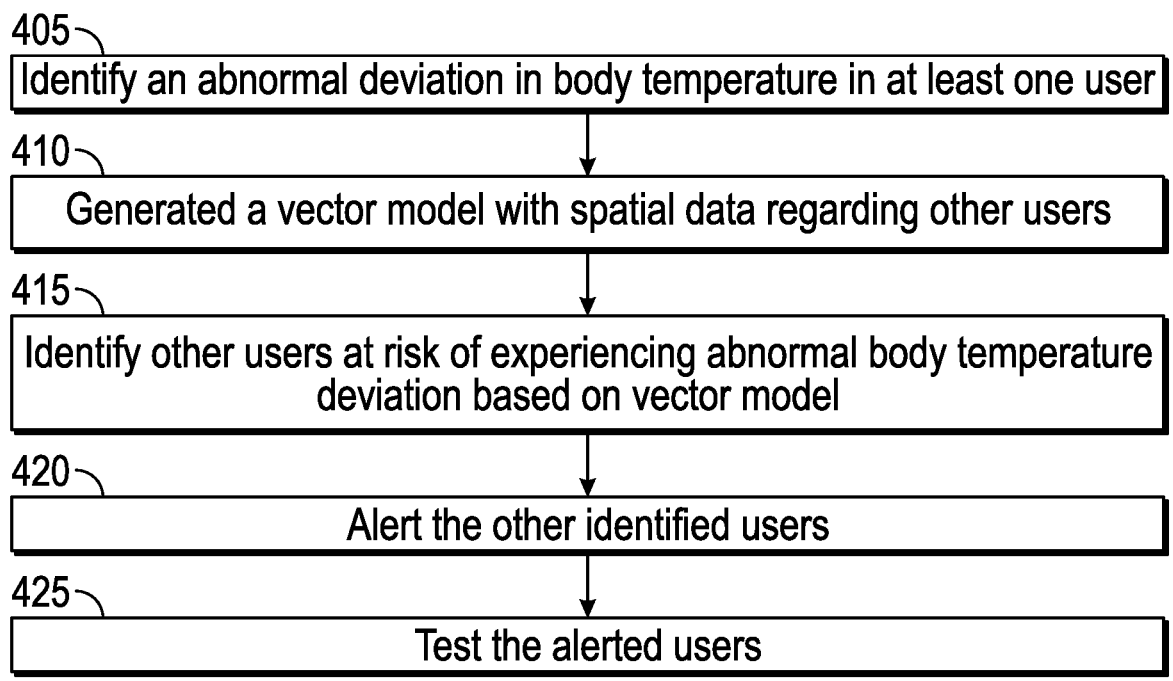
FIG. 4 is a flow chart of reporting and monitoring according to another embodiment.

In addition to focusing on individual users using the body temperature detection system comprising a wearable device 100, a mobile device 220, and a server 240, the detection system can be applied to multiple users that are located in close proximity for an extended amount of time. Through a series of aggregate analyses, the system can increase the predictability of temperate spike events or other abnormal body temperature deviations in the local area. FIG. 4 is a flow chart for tracking body temperature of multiple users in a local area according to an embodiment.

As shown in FIG. 4, an abnormal deviation in body temperature is identified in at least one user (step 405). The detection can be determined in the same manner as explained with respect to FIG. 3. Once the abnormal deviation in an individual user is identified, a vector model is generated with spatial data regarding the other users (step 410). The spatial data can be, for example, a seating arrangement at a concert venue, stadium seating layouts, office locations, cabin assignments, room numbers, or other information or data that identifies positions or locations of other users in the local area. Based on the spatial data, the vector model can predict which other users could also be potentially at risk of experiencing a temperature spike event or other abnormal body temperature deviation (step 415). In particular, the vector model is designed in such a way as to look at the spatial data, such as a ship, the seating plan in a stadium, or seating arrangement in a concert venue, to be able to identify clusters of potential infections. For example, if there were eight people at a dining table on a cruise ship or six line workers at a packaging plant, and a known percentage were either infected with Covid or had a noticeable spike or abnormal deviation in body temperature, then server 240 could alert the employer or host that guests or other worker in close proximity would need to potentially be tested. Determining what other guests or employees may be affected can be based on a distance threshold from the user with the abnormal body temperature deviation, such as 1 meter, 2 meters, 5, meters, or any other distance as may be reasonable to ensure all potentially affected other guests or employees can be identified.

This predictive data can be used to alert those other users (step 420) and enable those alerted users to be tested precautionarily for the illness, such as a virus, before symptoms appear (step 425). For example, server 240 could send an alert signal to each of the identified users that can be displayed on the user's wearable device 100 or on the user's mobile device 220 and provide instructions to the users to seek medical assistance for testing.

To facilitate and generate accurate spatial data among the users in the local area, a registration process can require each user through their wearable device 100 or mobile device 220 to provide the user's seating assignment, cabin room number, dining room/table assignment, or other relevant location information. The employer or host can also provide diagrams of these locations showing their spatial relationship to each other. For example, the employer or host can upload seating charts, office charts, cabin layout charts, dining table layouts and assignments or any other relevant location information to the server 240 to enable the analyses of spatial data.

Through this system, the employer or host can be aware of the body temperature of everyone in a local area, such as on a cruise ship, in a concert venue, in an office, in a sports arena, or in a factory line. And based on detecting one or more users having a detected abnormal body temperature deviation, the system can identify other users who may be affected based on the spatial data. Through bidirectional messaging and voice capabilities, all of these other users can be contacted, such as by server 240 sending a message to application 222 running on the user's mobile device 220 to have those users tested and/or quarantined.

To make this identification process more effective, all datasets for all venues from a specific employer or host can be fed into a deep structured learning model that is continuously updated with real-time data. The deep structured learning model can be configured in a manner analogous to clinical data models that take medical records as input to predict cancer outcomes. In this case, the deep structured learning model is designed to identify individual users that have a higher-than-normal probability to experience an abnormal body temperature deviation in the near future.

As already explained in relation to FIGS. 3 and 4, if an individual's temperature data shows an abnormal body temperature deviation or one of the models predicts such a deviation, server 240 can send an alert signal to the affected user by sending the signal to the wearable device 100 and/or mobile device 220. The server 240 can then initiate asking the user a series of questions to determine if there is a reasonable explanation for the user's increased temperature. For example, the user could be asked if they are participating in a strenuous activity, such as a tennis game, if they are outside in direct sunlight, of if they are in a confined space that has an elevated ambient temperature, like a kitchen or spa. In addition, the employer or host can provide the system with additional items to ask the user that are specific for each venue.

These questions and addition items can be stored in the database 244 and used to construct finite state automata (FSA) to drive the mechanics of the interactions with the relevant user. If the outcome of the FSA reaches a known good state, then the user is informed that their abnormal body temperature deviation is not likely a possible infection at this time. If the outcome of the FSA reaches any other state, then the user is directed to contact the venue's medical personnel for further examination. At the same time, server 240 can notify the employer or host to enable medical personnel to be alerted of the situation. If there are additional steps to follow, the employer or host can also define additional steps or protocols for this venue, and server 240 can initiate those steps. For example, a cruise ship operator could establish a protocol that is provided to server 240 that specifies, per user or per cabin, which sickbay a user should attempt to reach and which ship's doctor to whom to report. The protocol could also direct server 240 to establish a voice call between the user and medical intake personnel.

The system of FIG. 2 and processes of FIGS. 3 and 4 are designed to provide each employer or host relevant data about the users' conditions. Server 240 can also provide data about the results generated by the data models as they are produced. Typically, an employer or host can use a computing device to contact server 240 and make queries about a specific user or a specific venue, such as by using a REST API. This API can allow the employer or host to update the server 240 with certain details, such as cancellations, extensions of time, etc. The employer or hosts can also designate a particular server 240, or set of servers 240, with which to communicate.

In addition, the employer or host can elect to receive a stream of real-time data that reflects the current state of the users and venues that are sent to server 240. These data can include the processed data for a specific user or set of users, as well as the data results produced by the data models for a specific venue or set of venues. Another interaction between the system and employers or hosts is the specification of protocols to follow in the event a temperature event (e.g., detection of an abnormal body temperature deviation in one or more users) is detected by the sensor data or predicted by a data model. An employer or host can start with a default set of protocols designed to catch the typical types of temperature spikes in body temperature or other abnormal body temperature deviations. These protocols can be modified and customized to be as specific as the employer or host cares to make them to tailor the protocol to a particular venue. As a result, the employer or host maintains full discretion in making the decisions relating to the treatment of their own employees or guests.

Each protocol can be uploaded into the application 242 and/or database 244 before an event takes place. A set of configuration records directs the server 240 to follow a specific set of actions during a temperature event. This set of actions can be represented as a finite state automaton, or FSA. Each event that takes place causes the FSA to change state, and each state in the FSA algorithm can direct the server 240 to take a specific action. Since the FSA is deterministic, the order and timing of events can be specified exactly.

The protocol can drive a robust set of user interactions. For example, it can direct the server 240 to have the application 222 place a notification on the user's mobile device 220 with messages specific to the state of the FSA. It can further direct server 240 to send the users SMS messages and retrieve responses sent back to the server 240 by the user. Typically, these would be questions and answers used to rule out infections. The protocol can also direct server 240 to initiate an automated Interactive Voice Response (IVR) VoIP call to the user's mobile device 220. Typically, an IVR is used when the user fails to respond to SMS messages in a timely manner. An IVR can also be used when direct communication is required with the user because of time constraints. The IVR can rapidly step the user through a series of questions, such as less than 2 minutes. Server 240 can also initiate a live, in-person call between the user and medical personnel specified by the protocol, which allows a medical professional to consult directly with the user and make a determination regarding the steps a user should follow.

As shown in FIG. 2, the system includes a hardware temperature sensor built into wearable device, such as a bracelet or a watch, that can provide body temperature data to a reader (e.g., mobile device 220) through a wireless protocol, an application running on a mobile device such as a smartphone that can function as a reader and also communicate through the internet, and a software system running on a cluster of servers that accepts temperature data reported by the mobile device running the application to make determinations about potential infection events.

When the wearable device is implemented with NFC, the mobile device can read the body temperature data when the wearable device is brought in close proximity to the mobile device for the application to read. When implemented with Bluetooth, the wearable device can send data continuously to the application on the mobile device.

The application (e.g., application 222 on mobile device 220) can serve as a bridge between the body temperature data read from the wearable device and the server. The application can accept timestamped data, as well as location and user identifiers, and forward the data to the server. It can also present the user with informational notifications as directed by the server. Additionally, it can present a series of questions to the user as directed by the server to allow the server to gather more information before making a determination about a potential infection event.

The server can include a cluster of server machines, routers, voice gateways, and databases that accept incoming body temperature data (as well as related data including time, location, and user identity), process the data through customer-defined protocols and internally built data models, and use the results to make a determination if a user has a possible infection that should be examined by qualified medical personnel. The server can follow an established protocol to either rule out the possible infection or safely get the user to an employer or host's designated medical personnel.

The software on the server (e.g., application 242) can include a set of coroutines, well-defined API's, databases (e.g., database 244), and message queues that implement the logic and processes of the system. The data front-end can be a REST interface that accepts incoming time-stamped body temperature measurements from the users' wearable devices along with other related data including, for example, location and user identity. The front-end handles security handling and preliminary data checking and passes the data packets into input queues for different parallel lines of processing. The input queues can also be configured to send each data packet to an employer or host defined testing service, several data models, and a database back-end store. The employer- or host-defined testing service passes each data measurement though the baseline model constructed for each user to determine if a user's temperature has exceeded the employer or hosts specified maximum.

The data models can be used to make statistical predictions of various types for each individual user, and in several cases, about the users in aggregate for a venue or employer/host. The system can operate all of these elements simultaneously to provide an accurate, robust, and scalable architecture.

When a temperature event (e.g., an abnormal body temperature deviation) has occurred for a particular user, the server follows the specified protocol for the user at the current venue. The server first notifies the user about the event though the application on the user's mobile device. The server can use SMS messaging to implement a dialog with the user to gather more information before making a final determination that the user has a possible infection. If the user fails to respond to the SMS messages, the server can place a VoIP IVR call to the user to gather the needed information. If the user fails to answer these calls, the server can place the user in direct voice contact with designated medical personnel to make the actual determination.

If the user responds to the SMS messages, the protocol provided by the employer or host may determine that the likelihood of a possible infection is low. In that case, the server can inform the user of this determination and close and log the event. But if the protocol provided by the employer or host determines that the likelihood of a possible infection is high, the server can follow the part of the protocol specifying which steps are to be followed to get the user safely to a designated medical facility for testing and evaluation. For example, a user on a cruise ship can be instructed to report to a specific sickbay located on the same deck as the user's cabin. If the user reports an inability to get to the designated medical facility, the protocol can instruct the user to remain in the user's cabin and send a message to the medical office informing them to send someone to the user's cabin to make an evaluation.

The server can also feed all received data into several predictive models. These models make statistical predictions based on historical data from the database storing the received data. The models for venues with large gatherings of people can include spatial data uploaded by the employer or host so that the models can make statistical predictions based on the spatial relationship between a user with a confirmed abnormal body temperature deviation and other users in close proximity to that user. For example, if one user on a cruise ship has a confirmed temperature event, the users seated nearby at that user's dining table can be asked to come into the sickbay for testing.

Various embodiments of the invention are contemplated in addition to those disclosed herein above. The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

The invention claimed is:

1. A wearable device, comprising:
   a temperature sensor configured to detect a body temperature of a user wearing the wearable device and produce a temperature signal representative of the detected body temperature;
   a transmitter configured to send and receive signals including the temperature signal produced by the temperature sensor;
   circuitry coupled to the temperature sensor and the transmitter; and
   a memory coupled to the circuitry comprising a plurality of instructions that, when executed by the circuitry, cause the wearable device to:
   receive a plurality of temperature signals from the temperature sensor over a predetermined period of time;
   transmit the plurality of temperature signals to a server to determine a baseline temperature pattern for the user;
   receive a current temperature signal from the temperature sensor;
   transmit the current temperature signal to the server;
   receive a user alert signal from the server when the current temperature signal differs from the baseline temperature pattern by a predetermined threshold, the user alert signal indicating a potential illness of the user; and
   receive a proximity alert signal from the server when a current temperature signal of a different user located within a predetermined distance from the user differs from a baseline temperature pattern of the different user by a predetermined threshold.

2. The wearable device of claim 1, the memory further comprising an instruction executed by the circuitry to cause the wearable device to transmit location information of the user and an identifier associated with the user in combination with the current temperature signal.

3. The wearable device of claim 1, wherein the wearable device is a bracelet configured to fit around and be worn around a wrist of the user.

4. The wearable device of claim 1, wherein the transmitter is configured to transmit signals to an application running on a mobile device; and
   wherein the transmitter communicates with the mobile device using Nearfield Communication or Bluetooth when the wearable device is located nearby to the mobile device.

5. The wearable device of claim 1, the memory further comprising an instruction executed by the circuitry to cause the wearable device to receive body temperature data and confidence values from sensors built into the circuitry.

6. The wearable device of claim 1, the memory further comprising an instruction executed by the circuitry to cause the wearable device to display temperature information and diagnostic messages to the user.

7. The wearable device of claim 1, wherein the wearable device further comprises an RFID circuit, and
   wherein the memory further comprises an instruction executed by the circuitry to cause the RFID circuit in the wearable device to share location and identification information with an RFID reader located in a venue.

8. The wearable device of claim 1, the memory further comprising an instruction executed by the circuitry to cause the wearable device to serve as an alert beacon in response to the alert signal.

9. The wearable device of claim 1, wherein the wearable device further comprises a display, and
   wherein the memory further comprises an instruction executed by the circuitry to receive informational messages from the server and to display the received informational messages on the display of the wearable device.

10. A method for detecting an abnormal body temperature deviation in a user, the method comprising:
    detecting a plurality of body temperatures of a user from a temperature sensor on a wearable device worn by the user;
    producing a temperature signal for each of the detected plurality of body temperatures, each temperature signal being representative of a corresponding one of the plurality of detected body temperatures;
    transmitting the temperature signals to a server to determine a baseline temperature pattern for the user;
    receiving a current temperature signal from the temperature sensor;
    transmitting the current temperature signal to the server;
    receiving a user alert signal from the server when the current temperature signal differs from the baseline temperature pattern by a predetermined threshold, the user alert signal indicating a potential illness of the user; and
    receiving a proximity alert signal from the server when a current temperature signal of a different user located within a predetermined distance from the user differs from a baseline temperature pattern of the different user by a predetermined threshold.

11. The method of claim 10, the method further comprising transmitting location information of the user and an identifier associated with the user in combination with the current temperature signal.

12. The method of claim 10, wherein the wearable device is a bracelet configured to fit around and be worn around a wrist of the user.

13. The method of claim 10, the method further comprising transmitting signals to an application running on a mobile device using Nearfield Communication or Bluetooth when the wearable device is located nearby to the mobile device.

14. The method of claim 10, the method further comprising receiving body temperature data and confidence values from sensors built into circuitry in the wearable device.

15. The method of claim 10, the method further comprising displaying temperature information and diagnostic messages to the user.

16. The method of claim 10, wherein the wearable device further comprises an RFID circuit, and
   wherein the method further comprises causing the RFID circuit in the wearable device to share location and identification information with an RFID reader located in a venue.

17. The method of claim 10, the method further comprising causing the wearable device to serve as an alert beacon in response to the alert signal.

18. The method of claim 10, wherein the wearable device further comprises a display, and
   wherein the method further comprises receiving informational messages from the server and displaying the received informational messages on the display of the wearable device.

\* \* \* \* \*